United States Patent [19]

Matsuyama et al.

[11] Patent Number: 5,126,248
[45] Date of Patent: Jun. 30, 1992

[54] PROCESS FOR PREPARATION OF RIBOFLAVIN

[75] Inventors: Akinobu Matsuyama, Himeji; Kimitoshi Kawai, Hyogo; Sadao Kageyama, Himeji; Shoichi Takao, Sapporo, all of Japan

[73] Assignee: Daicel Chemical Industries, Ltd., Osaka, Japan

[21] Appl. No.: 393,868

[22] Filed: Aug. 11, 1989

Related U.S. Application Data

[63] Continuation of Ser. No. 883,796, Jul. 9, 1986, abandoned.

[30] Foreign Application Priority Data

Jul. 29, 1985 [JP] Japan .................................. 60-167260
Feb. 5, 1986 [JP] Japan .................................. 61-23486

[51] Int. Cl.$^5$ ....................... C12P 25/00; C12N 15/00; C12N 1/16; C12N 1/18

[52] U.S. Cl. ................................... 435/66; 435/172.1; 435/255; 435/256; 435/942

[58] Field of Search ...................... 435/66, 172, 85, 86, 435/119, 146, 255, 256, 942

[56] References Cited

FOREIGN PATENT DOCUMENTS 0137226 8/1984 European Pat. Off. .............. 435/66

Primary Examiner—Irene Marx
Attorney, Agent, or Firm—Flynn, Thiel, Boutell & Tanis

[57] ABSTRACT

Riboflavin is effectively obtained by culturing in a medium (1) a purine-requiring revertant derived from a riboflavin-producing yeast which belongs to the genus Saccharomyces and has a purine requirement or (2) a riboflavin-producing yeast which belongs to the genus Saccharomyces and is resistant to ammonium ion, and collecting the produced riboflavin.

10 Claims, No Drawings

PROCESS FOR PREPARATION OF RIBOFLAVIN

This application is a continuation of U.S. Ser. No. 06/883,796, filed Jul. 9, 1986 now abandoned.

The invention relates to a process for production of riboflavin by fermentation. More particularly, it concerns a process for the preparation of riboflavin by culturing a riboflavin-producing yeast belonging to Saccharomyces or a variant of that genus.

According to the process of the present invention, riboflavin can be efficiently produced through fermentation with the use of acetic acid as a carbon source.

Riboflavin is useful as, for example, a pharmaceutical compound, an additive for feed and a colorant for food.

STATEMENT OF PRIOR ART

Conventional processes for the production of riboflavin through fermentation comprise culturing, for example, *Eremothecium ashbyii*, *Ashbya gossypii*, *Candida flareri* or *Clostridium acetobutylicum* in a sugar medium to thereby produce and accumulate riboflavin in the culturing broth (cf. Progress Industrial Microbiology, vol. 1, p. 139 (1959)).

Some of us have previously reported a process for the production of riboflavin through fermentation wherein acetic acid is employed as a carbon source (cf. Agr. Biol. Chem., 28, 559, 566 and 765 (1964)).

In the U.S. patent application Ser. No. 643,226, corresponding to EPC patent application No. 84 109 683.7, there is disclosed a fermentation method using a variant such as a purine-requiring variant belonging to the genus Saccharomyces and 3-amino-1,2,4-triazole-resistant variant belonging to the same genus.

In the above literature, a name *Candida robusta* is used to represent a fungus. However, subsequent studies has revealed that a type strain of *C. robusta* has spores. Thus Lodder has reclassified *C. robusta* into *Saccharomyces cerevisiae* (cf. The Yeast, ed. 1970).

However no spores are observed in the strain used in the above literature. Therefore, it seems to be an asporogenic type of *S. cerevisiae*. Thus, it is called *S. cerevisiae* (*C. robusta*) in the present specification.

Although the abovementioned fungi are known, there have been still many problems to be solved in the production of riboflavin through fermentation in an industrial scale. That is, it is required to obtain a fungus which rapidly produces riboflavin and accumulates the same at a high concentration. When using a known auxotrophic fungus, it is necessary to add an expensive material required thereby to a medium. Thus, it is very important from an industrial viewpoint to lower the amount of the required material to be added or to make the same unnecessary.

From this point of view, the present invention aims at obtaining a fungus having a high riboflavin-productivity and to provide a novel process for the production of riboflavin with the use of the same.

Further, there is a problem in the production of riboflavin through fermentation with the use of a riboflavin-producing fungus belonging to the genus Saccharomyces in that the fungus is so sensitive to an ammonium ion liberated from a nitrogen source in the medium that the accumulation of riboflavin and the growth of the fungus are extremely lowered at an ammonium ion concentration of, for example, 2000 ppm or above.

From this point of view, the present invention aims at providing a novel and improved process for the industrial production of riboflavin with the use of a strain which shows little decrease in the accumulation of riboflavin even at an ammonium ion concentration in the medium of 2000 ppm or above.

SUMMARY OF THE INVENTION

The process cf the invention is effected with the use of one of the below defined fungus, in particular, a yeast.

A process for preparing riboflavin, according to the invention, comprises the steps of culturing in a cultivation medium, (1) a purine-requiring revertant derived from a riboflavin-producing yeast which belongs to the genus *Saccharomyces* and has the purine requirement or (2) a riboflavin-producing yeast which belongs to the genus *Saccharomyces* and is resistant to ammonium ion, and collecting the produced riboflavin.

The invention includes two embodiments. One in which the yeast (1) used produces riboflavin at a relatively high rate and at a high concentration and requires no additional material which may be expensive.

The other embodiment uses yeast (2) which produces riboflavin without decreased accumulation when a concentration of ammonium ion has been increased in the culturing medium.

The invention will be below illustrated in respect to these two embodiments.

EMBODIMENT FOR THE YEAST (1)

Any purine-requiring revertant may be employed in the present invention so long as it is derived from a riboflavin-producing fungus which belongs to the genus Saccharomyces and has a purine-requirement.

A preferable example of the same is *Saccharomyces cerevisiae* TR-29 (FERM No. 782). This is a purine-requiring revertant resistant to 3-amino-1,2,4-triazole which is derived from a parent strain of a purine-requiring and 3-amino-1,2,4-triazole-resistant strain TP-1010 (FERM BP-565) by a conventional method through N-methyl-N'-nitro-N-nitrosoguanidine treatment. Since the TR-29 strain shows reversed purine-requirement, it is distinguishable from the parent strain, i.e., TP-1010.

Method for Obtaining the Strain

The strain used in the present invention may be readily obtained by employing a purine-requiring and riboflavin-producing fungus belonging to the genus Saccharomyces as a parent strain and treating the same in a conventional manner to induce variation.

For example, *S. cerevisiae* TP-1010, which is a 3-amino-1,2,4-triazole-resistant and purine-requiring strain used as a parent strain, is irradiated with ultraviolet light or treated with a chemical such as N-methyl-N'-nitro-N-nitrosoguanidine and cultured in a minimum medium free from purines as shown in Table 1. Then the colonies thus grown are selected as a purine-requiring revertant which is resistant to 3-amino-1,2,4-triazole.

TABLE 1

| Composition of minimum medium | |
|---|---|
| Component | Concentration |
| glucose | 20 g/l |
| $(NH_4)_2SO_4$ | 2 g/l |
| $MgSO_4.7H_2O$ | 0.5 g/l |
| $KH_2PO_4$ | 1.5 g/l |
| biotin | 2 μg/l |
| 3-amino-1,2,4-triazole | 50 mM |
| agar | 15 g/l |

TABLE 1-continued

| Composition of minimum medium | |
|---|---|
| Component | Concentration |
| pH | 6.0 |

The reversion of purine-requirement of the variant thus obtained may be confirmed by the following growth test.

S. cerevisiae TP-1010, which is the parent strain, the purine-requiring revertant derived therefrom and S. cerevisiae TR-29 are each smeared on the medium as shown in Table 1 and on another medium prepared by adding 0.1% of adenine to the former and cultured therein at 30° C. for one week to thereby observe the growth of the same. Table 2 shows the result

TABLE 2

| | TR-1010 (3-amino-1,2,4-triazole resistant, purine-requiring) | TR-29 (3-amino-1,2,4-triazole resistant, reversed, purine-requiring) |
|---|---|---|
| minimum medium | − | + |
| minimum medium +0.1% adenine | + | + |

+: enough growth.
−: no growth.

Table 2 proves that S. cerevisiae TR-29 has obviously no purine-requirement, which suggests the reversion of the same.

Culture Method

The microorganism employed in the present invention is cultured in the following manner. Examples of the carbon source therefor are organic acids such as acetic or gluconic acid, sugars such as glucose, sucrose or xylose and alcohols such as ethanol or glycerol.

Examples of the nitrogen source therefor are various nitrogen compounds such as ammonium sulfate, ammonium chloride, ammonium carbonate, urea, amino acids or polypeptone.

In addition to the carbon and nitrogen sources, it is preferable to use inorganic salts such as potassium phosphate or magnesium sulfate. Furthermore, trace nutrients including vitamins such as biotin, amino acids or nucleic acid bases optionally added, if required, may accelerate the accumulation of riboflavin. The invention may apply to a method for producing riboflavin by adding zinc ion to the cultivation system to increase the productivity of riboflavin and prevent the inhibition effect due to an iron ion therein.

The culturing is preferably carried out under aerobic conditions. The pH value of the medium lies within the range of 2 to 10. The most preferable result can be obtained by adjusting the pH value to 6 to 9. The culturing may be carried out at a temperature suitable for the growth of the fungus to be used and for the production of riboflavin within the range of 20° to 37° C.

Riboflavin can be collected from the culturing broth thus obtained in a known manner. That is, the culturing broth is heated to 60° to 120° C. to thereby dissolve riboflavin and centrifuged to separate yeast cells from the filtrate. The filtrate may be concentrated if necessary and then reduced with hydrosulfite or titanium trichloride to thereby precipitate riboflavin. The riboflavin thus obtained may be purified by oxidation in the atmosphere and recrystalization from a solvent, e.g., water or an aqueous solution of acetic acid.

Riboflavin may be purified by forming a hot water solution of the product mixture of the riboflavin fermentation according to the invention, separating solid matters such as fungus therefrom it and obtaining riboflavin from the solution with crystallization. This method produces riboflavin with a very high purity.

EMBODIMENT FOR YEAST (2)

The term, "ammonium ion-resistant" as used herein means resistance against a material which liberates ar ammonium ion in the medium. Examples of such a material are ammonium salts such as ammonium chloride, ammonium sulfate, ammonium nitrate, ammonium acetate or ammonium fumarate, ammonia water and urea.

Microorganism to be Employed

Any ammonium-resistant variant may be used in the present invention so long as it is derived from a riboflavin-producing fungus belonging to the genus Saccharomyces.

A preferable example of the same is Saccharomyces cerevisiae NH-268 (FERM BP-965). This is an ammonium ion-resistant and 3-amino-1,2,4-triazole-resistant variant derived from a parent strain of a 3-amino-1,2,4-triazole-resistant and purine-requiring revertant TR-29 (FERM BP-782) by a conventional method through N-methyl-N'-nitro-N-nitrosoguanidine treatment. Since the NH-268 shows ammonium ion resistance, it is distinguishable from the parent strain.

Method for obtaining the Strain

The strain used in the present invention may be readily obtained by employing a purine-requiring and riboflavin-producing fungus belonging to the genus Saccharomyces as a parent strain and treating the same in a conventional manner to induce variation.

For example, S. cerevisiae TR-29, which is a 3-amino-1,2,4-triazole-resistant and purine-requiring revertant, is irradiated with ultraviolet light or treated with a chemical such as N-methyl-N'-nitro-N-nitrosoguanidine and smeared on an agar medium containing an ammonium ion at a high concentration as shown in Table 3 and colonies thus grown are selected as an ammonium ion-resistant strain.

TABLE 3

| Composition of selective medium | |
|---|---|
| Component | Concentration |
| acetic acid | 20 g/l |
| $(NH_4)_2SO_4$ | 50 g/l |
| $MgSO_4 \cdot 7H_2O$ | 0.5 g/l |
| $KH_2PO_4$ | 1.5 g/l |
| biotin | 2 µg/l |
| yeast extract | 1.0 g/l |
| agar | 15 g/l |
| pH | 7.0 |

The ammonium ion-resistance of the variant thus obtained may be confirmed by the following growth test.

S. cerevisiae TR-29, which is the parent strain, and the ammonium ion-resistant variant NH-268 derived therefrom are each inoculated on 100 ml of a liquid medium containing 2% of glucose, 0.5% of polypeptone, 0.3% of yeast extract and 0.3% of malt extract and cultured therein under shaking at 30° C. for 40 hours. The obtained culturing broth is inoculated into a medium as shown in Table 2 at a ratio of 12% and cultured therein under shaking at 30° C. for five days.

TABLE 4

| Component | Concentration |
|---|---|
| calcium acetate | 103 g/l |
| (NH4)2SO4 (or NH4Cl) | 5-10 (4-8) g/l |
| MgSO4.7H2O | 1 g/l |
| KH2PO4 | 2 g/l |
| ZnSO4.7H2O | 11 mg/l |
| pH | 7 |

The growth is determined from the optical density at 610 nm. Table 5 shows relative growth at various ammonium ion concentrations determined by regarding the growth at an ammonium ion concentration of 1350 ppm as 100. Table 5 suggests that S. cerevisiae NH-268 is obviously resistant to an ammonium ion.

TABLE 5

| | Relative growth | |
|---|---|---|
| (ammonium ion, ppm) | NH-268 | TR-29 |
| Ammonium sulfate | | |
| 1350 | 100 | 100 |
| 1620 | 74 | 62 |
| 2160 | 65 | 44 |
| 2700 | 45 | 27 |
| Ammonium chloride | | |
| 1350 | 100 | 100 |
| 1620 | 91 | 81 |
| 2160 | 66 | 55 |
| 2700 | 56 | 33 |

CULTURE METHOD

The microorganism employed in the present invention is cultured in the following manner. Examples of the carbon source therefor are organic acids such as acetic or gluconic acid, sugars such as glucose, sucrose or xylose and alcohols such as ethanol or glycerol.

Examples of the nitrogen source therefor are various nitrogen compounds such as ammonium sulfate, ammonium chloride, ammonium carbonate, urea, amino acids or polypeptone.

In addition to the carbon and nitrogen sources, it is preferable to use inorganic salts such as potassium phosphate or magnesium sulfate. Furthermore, trace nutrients including vitamins such as biotin, amino acids or nucleic acid bases optionally added, if required, may accelerate the accumulation of riboflavin. This embodiment may effectively apply to the method as before disclosed in which zinc ion is used.

The culturing is preferably carried out under aerobic conditions. The pH value of the medium lies within the range of 2 to 10. The most preferable result can be obtained by adjusting the pH value to 6 to 9. The culture may be carried out at a temperature suitable for the growth of the fungus to be used and for the production of riboflavin within the range of 20° to 37° C.

Riboflavin can be collected from the culturing broth thus obtained in a known manner. That is, the culturing broth is heated to 60° to 120° C. to thereby dissolve riboflavin and centrifuged to separate yeast cells from the filtrate. The filtrate may be concentrated if necessary and then reduced with hydrosulfite or titanium trichloride to thereby precipitate riboflavin. The riboflavin thus obtained may be purified by oxidization in the atmosphere and recrystalization from a solvent, e.g., water or an aqueous solution of acetic acid.

In the same way as shown before, riboflavin produced in the embodiment can be purified with a hot water solution thereof and crystallization.

EXAMPLE 1

S. cerevisiae TR-29 and S. cerevisae TR-1010, which was the parent strain of the former, were each inoculated into 100 ml of a preculture medium containing 2% of glucose, 0.5% of polypeptone, 0.3% of yeast extract and 0.3% of malt extract and cultured therein under shaking at 30° C. for 37 hours. The preculturing broth was inoculated into a fermentation medium as shown in Table 6 at a ratio of 10% and cultured therein under shaking at 30° C. for ten days. In the case of S. cerevisiae TP-1010, i.e., the parent strain, the amount of riboflavin accumulated in the culturing broth was 2.56 g/l. On the other hand, the amount observed in the case of S. cerevisiae TR-29 was 2.79 g/l, showing an increase. Furthermore, it was unnecessary to add purines, which were required materials, to the medium in the latter case.

EXAMPLE 2

S. cerevisiae TR-29 was cultured in the same fermentation medium as the one shown in Table 6, except the medium contained 132 g/l of calcium acetate and 6 g/l of ammonium sulfate for eight days in the same manner as described in Example 1.

As a result, 3.02 g/l of riboflavin was accumulated in the culturing broth.

TABLE 6

| Composition of fermentation medium | |
|---|---|
| calcium acetate | 103 g/l |
| (NH4)2SO4 | 4 g/l |
| KH2PO4 | 2 g/l |
| MgSO4.7H2O | 1 g/l |
| ZnSO4.7H2O | 2.2 mg/l |
| adenine* | 1 g/l |
| pH | 7.0 |

*added only in the case of TP-1010.

EXAMPLE 3

S. cerevisiae NH-268 and S. cerevisiae TR-29, which was the parent strain of the former, where each inoculated into 100 ml of a liquid medium containing 2% of glucose, 0.5% of polypeptone, 0.3% of yeast extract and 0.3% of malt extract and cultured therein under shaking at 30° C. for 40 hours. The preculturing broth was inoculated into a fermentation medium as shown in Table 7 at a ratio of 16% and cultured therein under shaking at 30° C. for 11 days. In the case of S. cerevisiae TR-29, i.e., the parent strain, the amount of riboflavin accumulated in the culturing broth was 3.10 g/l. On the other hand, the amount observed in the case of S. cerevisiae NH-268 was 3.40 g/l, showing an increase.

TABLE 7

| Composition of fermentation medium for producing riboflavin | |
|---|---|
| Component | Concentration |
| calcium acetate | 132 g/l |
| (NH4)2SO4 | 6 g/l |
| MgSO4.7H2O | 1 g/l |
| KH2PO4 | 2 g/l |
| ZnSO4.7H2O | 11 mg/l |
| pH | 7 |

EXAMPLE 4

The same strains as those used in Example 3 were cultured in the same manner as the one described therein except that the ammonium sulfate concentration of the fermentation medium was varied as shown in Table 8 for ten days. As shown in Table 8, *S. cerevisiae* NH-268 showed little decrease in the amount of riboflavin accumulated in the culturing broth with an increase in the ammonium ion concentration, compared with the case of the parent strain, i.e., *S. cerevisiae* TR-29.

TABLE 8

| Ammonium ion, ppm (ammonium sulfate, g/l) | Accumulated riboflavin (g/l) | |
|---|---|---|
| | TR-29 | NH-268 |
| 1890 (7) | 2.69 | 2.80 |
| 2160 (8) | 0.87 | 2.18 |
| 2430 (9) | 0.46 | 2.20 |

The embodiments of the invention in which an exclusive property or privilege is claimed are defined as follows:

1. A process for preparing riboflavin, which comprises steps of culturing in a cultivation medium (1) a purine-requiring revertant yeast, *Saccharomyces cerevisiae* TR-29, which is resistant to 3-amino-1,2,4-triazole and is derived from a riboflavin-producing parent yeast strain, *Saccharomyces cerevisiae* TP-1010, which has a purine requirement and is resistant to 3-amino-1,2,4-triazole, or (2) *Saccharomyces cerevisiae* NH-268, which is an ammonium ion and 3-amino-1,2,4-triazole-resistant variant derived from *Saccharomyces cerevisiae* TR-29, and collecting the produced riboflavin.

2. A process as claimed in claim 1, in which *Saccharomyces cerevisiae* TR-29 is used.

3. A process as claimed in claim 1, in which *Saccharomyces cerevisiae* NH-268 is used.

4. A process as claimed in claim 2, in which said *Saccharomyces cerevisiae* TR-29 is obtained by treating *Saccharomyces cerevisiae* TP-1010 with N-methyl-N'-nitro-N-nitrosoguanidine.

5. A process as claimed in claim 3, in which said *Saccharomyces cerevisiae* NH-268 is obtained by treating *Saccharomyces cerevisiae* TR-29 with N-methyl-N'-nitro-N-nitrosoguanidine.

6. A process as claimed in claim 2, in which said *Saccharomyces cerevisiae* TR-29 is cultured under aerobic conditions in a culture medium having a pH of 6 to 9 at a temperature of 20° C. to 37° C., said culture medium containing a member selected from the group consisting of a carbon source, a nitrogen source, an inorganic salt, a vitamin, a zinc ion source, and mixtures thereof.

7. A process as claimed in claim 3, in which said *Saccharomyces cerevisiae* NH-268 is cultured under aerobic conditions in a culture medium having a pH of 6 to 9 at a temperature of 20° C. to 37° C., said culture medium containing a member selected from the group consisting of a carbon source, a nitrogen source, an inorganic salt, a vitamin, a zinc ion source, and mixtures thereof.

8. A process for preparing riboflavin, which comprises the steps of culturing in a cultivation medium having an ammonium ion concentration of 2000 ppm or above (1) a purine-requiring revertant yeast, *Saccharomyces cerevisiae* TR-29, which is resistant to 3-amino-1,2,4-triazole and is derived from a riboflavin producing parent yeast strain, *Saccharomyces cerevisiae* TP-1010, which has a purine requirement and is resistant to 3-amino-1,2,4-triazole, or (2) *Saccharomyces cerevisiae* NH-268, which is an ammonium ion and 3-amino-1,2,4-triazole-resistant variant derived from *Saccharomyces cerevisiae* TR-29, and collecting the produced riboflavin.

9. A process as claimed in claim 8, in which *Saccharomyces cerevisiae* TR-29 is used.

10. A process as claimed in claim 8, in which *Saccharomyces cerevisiae* NH-268 is used.

* * * * *